(12) United States Patent
Xing et al.

(10) Patent No.: US 9,087,626 B2
(45) Date of Patent: Jul. 21, 2015

(54) MEASURING MOISTURE IN A CNT BASED FLUID OR PASTE

(75) Inventors: Caihong Xing, Beijing (CN); Yunwang Mei, Beijing (CN); Yan Zhang, Beijing (CN); Haimei Zang, Beijing (CN); Gang Xu, Beijing (CN); Jun Ma, Irvine, CA (US)

(73) Assignee: CNANO TECHNOLOGY LIMITED, San Francisco, CA (US)

( * ) Notice: Subject to any disclaimer, the term of this patent is extended or adjusted under 35 U.S.C. 154(b) by 869 days.

(21) Appl. No.: 13/285,243

(22) Filed: Oct. 31, 2011

(65) Prior Publication Data

US 2013/0105741 A1 May 2, 2013

(51) Int. Cl.
*G01N 31/16* (2006.01)
*G01N 33/18* (2006.01)
*G01N 31/22* (2006.01)
*G01N 5/04* (2006.01)
*H01B 1/24* (2006.01)

(52) U.S. Cl.
CPC ................. *H01B 1/24* (2013.01); *G01N 5/045* (2013.01); *G01N 31/168* (2013.01); *G01N 31/222* (2013.01); *G01N 33/18* (2013.01)

(58) Field of Classification Search
None
See application file for complete search history.

(56) References Cited

U.S. PATENT DOCUMENTS

| | | | | |
|---|---|---|---|---|
| 3,679,638 A | * | 7/1972 | Korsgen | 528/486 |
| 6,815,207 B2 | * | 11/2004 | Yabuki et al. | 436/2 |
| 7,563,427 B2 | | 7/2009 | Wei | |
| 7,993,594 B2 | | 8/2011 | Wei | |
| 8,540,902 B2 | * | 9/2013 | Xing et al. | 252/511 |
| 2009/0208708 A1 | | 8/2009 | Wei | |
| 2009/0286675 A1 | | 11/2009 | Wei | |
| 2010/0026324 A1 | | 2/2010 | Camenzind | |
| 2010/0123079 A1 | | 5/2010 | Grace | |
| 2010/0300183 A1 | | 12/2010 | Dasher | |
| 2011/0006461 A1 | | 1/2011 | Dasher | |
| 2011/0171364 A1 | | 7/2011 | Xing | |
| 2011/0171371 A1 | | 7/2011 | Li | |
| 2011/0230672 A1 | | 9/2011 | Kang | |

OTHER PUBLICATIONS

Sturgeon, R. E. et al. "Determination of moisture content of single-wall carbon nanotubes," Anal Bioanal Chem (2012) 402:429-438; published online Nov. 29, 2011.*

* cited by examiner

*Primary Examiner* — Yelena G Gakh
*Assistant Examiner* — Michelle Adams
(74) *Attorney, Agent, or Firm* — Fernandez & Associates, LLP

(57) ABSTRACT

The present disclosure relates to pastes and methods of making a moisture determination of the paste during manufacture; optionally, the pastes comprise carbon nanotubes. The instant invention provides a simple and repeatable measurement protocol to determine the moisture or water content in paste comprising a non-aqueous solvent and a solid component, optionally, carbon nanotubes, CNT, and subsequently provide a method to monitor and control moisture level during electrode preparation and battery manufacturing.

10 Claims, No Drawings

MEASURING MOISTURE IN A CNT BASED FLUID OR PASTE

CROSS-REFERENCE TO RELATED APPLICATIONS

This application is related in part to U.S. Pat. Nos. 7,563,427, 7,993,594, U.S. 2009/0208708, U.S. 2009/0286675, U.S. 2011/0171364 and U.S. 2011/0171371; all incorporated herein in their entirety by reference.

BACKGROUND OF THE INVENTION

1. Field of the Invention

The present disclosure relates to pastes and methods of making a moisture determination of the paste during manufacture; optionally, the pastes comprise carbon nanotubes.

Carbon nanotubes (CNT) have many unique properties stemming from small sizes, cylindrical graphitic structure, and high aspect ratios. Carbon nanotubes possess outstanding material properties but are difficult to process and insoluble in most solvents. Historically polymers such as poly(vinylpyrrolidone) (PVP), poly(styrene sulfonate) (PSS), poly(phenylacetylene) (PAA), poly(meta-phenylenevinylene) (PmPV), polypyrrole (PPy), poly(p-phenylene benzobisoxazole) (PBO) and natural polymers have been used to wrap or coat carbon nanotubes and render them soluble in water or organic solvents. Previous work also reports single-walled carbon nanotubes (SWCNTs) have been dispersed with three types of amphiphilic materials in aqueous solutions: (i) an anionic aliphatic surfactant, sodium dodecyl sulfate (SDS), (ii) a cyclic lipopeptide biosurfactant, surfactin, and (iii) a water-soluble polymer, polyvinylpyrrolidone (PVP).

Conventional electro-conductive pastes are comprised primarily of polymeric binders which contain or have mixed in various amounts of electro-conductive filler such as finely divided particles of metal such as silver, gold, copper, nickel, palladium or platinum and/or carbonaceous materials like carbon black or graphite, and a liquid vehicle. A polymeric binder may attach the conductive filler to a substrate and/or hold the electro-conductive filler in a conductive pattern which serves as a conductive circuit. The liquid vehicle includes solvents (e.g., liquids which dissolve the solid components) as well as non-solvents (e.g., liquids which do not dissolve the solid components). The liquid vehicle serves as a carrier to help apply or deposit the polymeric binder and electro-conductive filler onto certain substrates. It is very helpful to be able to measure and control the water content of a CNT-based paste.

BACKGROUND

Carbon nanotubes are a new class of conductive materials that can provide much enhanced performance for Lithium ion batteries. However, with the use of carbon nanotubes, the conventional cathode composition can no longer satisfy the requirement due to the specialty of carbon nanotubes versus carbon black. Typically, when carbon black was used as conductive filler in the cathode, the preferred composition is active material/conductive filler/binder is AM:90~97/CF:1~5/B:2~5, parts by weight. With carbon nanotubes, this composition will result in poor adhesion of cathode material on its current collector; alternatively, broken coatings when folded or wrapped. The instant invention discloses a method for measuring the moisture content of a fluid or paste that overcomes the deficiencies of the prior art.

Background and supporting technical information is found in the following references, all incorporated in their entirety herein by reference; U.S. Pat. No. 7,563,427, U.S.2009/0208708, U.S. 2009/0286675, U.S. 2010/0026324, U.S. 2010/0123079, U.S. 2010/0300183, U.S. 2011/0006461, U.S. 2011/0230672, U.S. 2011/0171371, U.S. 2011/0171364.

BRIEF SUMMARY OF THE INVENTION

Carbon nanotube-based paste is used in preparation of lithium ion battery electrodes. During electrode production, conductive paste is mixed with active cathode or anode materials, and then coated onto a current collector. The coating is then dried before further processed into battery format. The moisture content in the paste and electrode precursor is extremely important during electrode preparation. High moisture content may cause failure or damage in battery performance. The battery electrolyte can undergo hydrolyzing to form corrosive materials such as acidic hydrogen fluoride, which can cause severe problems for cathode material, current collector, and anyone who touches it if it leaks outside a failed battery. It is necessary to control and measure the moisture content in conductive pastes before going into final battery assembly.

The instant invention provides a simple and repeatable measurement protocol to determine the moisture or water content in paste comprising a non-aqueous solvent and a solid component, optionally, carbon nanotubes, CNT, and subsequently provide a method to monitor and control moisture level during electrode preparation and battery manufacturing.

DETAILED DESCRIPTION OF THE INVENTION

In preparation of pastes or other compounds, moisture, or water, may be present as adsorbed moisture at internal surfaces of nanotubes and as capillary condensed water in small channels. At low relative humidity's, moisture consists mainly of adsorbed water. At higher relative humidity's, liquid water becomes more and more important, depending on the pore size. Various solvents may deliquescent tendencies and absorb moisture from the air.

There are several methods of measuring moisture content in a given system, such as liquid evaporation, gas chromatography, Karl-Fischer titration, coulometric titration, volumetric titration. Karl Fischer titration is a classic titration method in analytical chemistry that uses coulometric or volumetric titration to determine trace amounts of water in a sample.

The main compartment of the titration cell contains the anode solution plus the analyte. The anode solution consists of an alcohol (ROH), a base (B), $SO_2$ and $I_2$. A typical alcohol that may be used is methanol or diethylene glycol monoethyl ether, and a common base is imidazole. The Pt anode generates $I_2$ when current is provided through the electric circuit. The net reaction is oxidation of $SO_2$ by $I_2$. One mole of $I_2$ is consumed for each mole of $H_2O$. In other words, 2 moles of electrons are consumed per mole of water. The major disadvantage is that the water has to be accessible and easily brought into methanol solution. Many common substances, especially foods such as chocolate, release water slowly and with difficulty, and require additional efforts to reliably bring the total water content into contact with the Karl Fischer reagents.

Carbon nanotube-based conductive paste has some unusual characteristics and behaviors as compared to other systems. Since CNTs often have high surface area, a paste often consists of large amounts of organic solvent, high viscosity, and poor flowability. Therefore, traditional measurement tools such as Karl-Fischer method can encounter severe problem when solvent is evaporated before reacting with a Karl Fischer reagent; a solvent can condense in the equipment causing large errors when in measured moisture content. Conductive carbon nanotubes may also interfere with Karl Fischer reaction if mixed with reagents.

The instant invention discloses the use of a second solvent, which is:
(1) miscible with the first solvent mixed with the particular CNT paste;
(2) Binders or dispersant that are used in the original paste are insoluble in the second solvent; thus carbon nanotubes precipitate when the second solvent is present in amounts exceeding more than about 25% by volume or weight of the total solvent mixture.
(3) the second solvent does not react with the selected Karl Fischer reagent, meaning no oxidation or reduction would occur between the second solvent and Karl Fisher reagent. By adding known amounts of second solvent to the paste, the moisture or water content can be extracted from the first solvent based into miscible solvent mixture and concentration can then be calculated based on total amount of the mixed solvent. The analysis is easier because CNTs are no longer in a dispersed state in the mixed solvent and further precipitate from such paste, leaving water inside the solvent rather than within the nanotubes or polymeric binders. Drawing a known amount of such mixed solvent and reacting with the Karl Fischer reagent determines the moisture content.

Preparation of Carbon Nanotubes Paste

Dispersant serves as an aid for dispersing carbon nanotubes in a solvent. It can be a polar polymeric compound, a surfactant, or high viscosity liquid such as mineral oil or wax. Dispersants used in the current invention include poly(vinylpyrrolidone) (PVP), poly(styrene sulfonate) (PSS), poly(phenylacetylene) (PAA), poly(meta-phenylenevinylene) (PmPV), polypyrrole (PPy), poly(p-phenylene benzobisoxazole) (PBO), natural polymers, amphiphilic materials in aqueous solutions, anionic aliphatic surfactant, sodium dodecyl sulfate (SDS), cyclic lipopeptide biosurfactant, surfactin, water-soluble polymers, poly(vinyl alcohol), PVA, sodium dodecyl sulfate, SDS, n-methylpyrrolidone, polyoxyethylene surfactant, poly(vinylidene fluoride), PVdF, carboxyl methyl cellulose (CMC), hydroxyl ethyl cellulose (HEC), polyacrylic acid (PAA), polyvinyl chloride (PVC) and combinations thereof. Polymeric binder choices include the dispersants mentioned as well as polyethylene, polypropylene, polyamide, polyurethane, polyvinyl chloride, polyvinylidene fluoride, thermoplastic polyester resin and combinations thereof.

Polyvinylpyrrolidone, PVP, binds polar molecules extremely well. Depending upon its molecular weight, PVP has different properties when used as a binder or as a dispersing agent such as a thickener. In some embodiments of the instant invention, molecular weights for dispersants and/or binders range between about 9,000 and 1,800,000 Daltons; in some embodiments, between about 50,000 to 1,400,000 Daltons are preferred; in some embodiments between about 55,000 to 80,000 Daltons are preferred.

Liquid Vehicle

A liquid vehicle, aqueous or non-aqueous, may serve as a carrier for carbon nanotubes. Liquid vehicles may be a solvent or a non-solvent, depending upon whether or not a vehicle dissolves solids which are mixed therein. The volatility of a liquid vehicle should not be so high that it vaporizes readily at relatively low temperatures and pressures such as room temperature and pressure, for instance, 25° C. and 1 atm. The volatility, however, should not be so low that a solvent does not vaporize somewhat during paste preparation. As used herein, "drying" or removal of excess liquid vehicle refers to promoting the volatilization of those components which can be substantially removed by baking, or vacuum baking or centrifuging or some other de-liquefying process at temperatures below 100 to 200° C.

In one embodiment, a liquid vehicle is used to dissolve polymeric dispersant(s) and entrain carbon nanotubes in order to render a composition that is easily applied to a substrate. Examples of liquid vehicles include, but are not limited to, water, alcohols, ethers, aromatic hydrocarbons, esters, ketones, n-methylpyrrolidone and mixtures thereof. In some cases, water is used as a solvent to dissolve polymers and form liquid vehicles. When combined with specific polymers these aqueous systems can replace solvent based inks while maintaining designated thixotropic properties, as disclosed in U.S. Pat. No. 4,427,820, incorporated herein in its entirety by reference.

Nanotube Dispersion

Dispersing carbon nanotubes in a liquid is difficult because of the entanglement of nanotubes into large agglomerates. Exemplary lithium ion battery active materials comprise lithium based compounds and/or mixtures comprising lithium and one or more elements chosen from a list consisting of oxygen, phosphorous, sulphur, nitrogen, nickel, cobalt, manganese, vanadium, silicon, carbon, aluminum, niobium and zirconium and iron. Typical cathode materials include lithium-metal oxides, such as $LiCoO_2$, $LiMn_2O_4$, and $Li(Ni_xMn_yCo_z)O_2]$, vanadium oxides, olivines, such as $LiFePO_4$, and rechargeable lithium oxides. Layered oxides containing cobalt and nickel are materials for lithium-ion batteries also. In some embodiments a fluoride based ion battery chemistry is employed.

Exemplary anode materials are lithium, carbon, graphite, lithium-alloying materials, intermetallics, and silicon and silicon based compounds such as silicon dioxide. Carbonaceous anodes comprising silicon and lithium are utilised anodic materials also. Methods of coating battery materials in combination with a carbon nanotube agglomerate onto anodic or cathodic backing plates such as aluminum or copper, for example, are disclosed as an alternative embodiment of the instant invention.

Dispersion of Carbon Nanotubes in n-Methyl Pyrrolidone.

30 grams of FloTube™ 9000 carbon nanotubes manufactured by CNano Technology Ltd. (Beijing, China), pulverized by jet-milling, were placed in 2-liter beaker. The tap density of this material is 0.03 g/mL. In another 500 milliliter beaker, 6 grams of PVP k90 (manufactured by BASF) was dissolved in 100 grams of n-methylpyrrolidone. Then the PVP solution was transferred to the nanotubes together with 864 grams n-methylpyrrolidone.

Electrode Paste Preparation

A PVDF solution was prepared by placing 10 g of PVDF (HSV900) and 100 g n-methyl pyrrolidone in a 500-mL beaker under constant agitation. After all PVDF was dissolved, designated amount of paste (Sample A) from Example 1 and PVDF solution were mixed under strong agitation of 500-1000 RPM for 30 minutes.

EXAMPLE 1

Measurement of Moisture Content in Several Organic Solvents

In a moisture-controlled environment, moisture contents of several solvents are measured via the Karl-Fischer method.

TABLE 1

|  | Test 1 (ppm) | Test 2 (ppm) | Test 3 (ppm) | Average value (ppm) |
|---|---|---|---|---|
| Ethyl Acetate | 26.1 ppm | 25.4 ppm | 37.6 ppm | 29.7 ppm |
| n-methyl pyrrolidone | 618 ppm | 611 ppm | 602 ppm | 610 ppm |
| Mixed Solvent of EA and nMP EA:nMP :: 5:1 by weight | 141 ppm | 136 ppm | 147 ppm | 142 ppm |

The average calculated moisture content for the mixed solvent, EA+nMP, is 126 ppm, calculated by adding $5/6^{th}$ of the EA moisture content to $1/6^{th}$ of the nMP moisture content; very close to the measured result of 142 ppm.

EXAMPLE 2

Measurement of moisture content in mixed solvent containing carbon nanotubes. A CNT-based paste was prepared using methods described in U.S.2011/0171364. Carbon nanotubes have been vacuum-dried prior to paste preparation. The measured moisture content using regular Karl-Fischer from nanotube powder is 3000 ppm.

TABLE 2

| Measurement Sequence | Test 1 (ppm) | Test 2 (ppm) | Test 3 (ppm) | Average value (ppm) |
|---|---|---|---|---|
| 1. nMP | 618 | 611 | 602 | 610 |
| 2. 0.1875 g dispersant + 14.0625 g nMP | 880 | 1004 | 988 | 960 |
| 3. Add 0.75 g CNT | 150 | 150 | 150 |  |
| 4. Add 75 g Ethyl Acetate | 203 | 218 | 215 | 212 |

The calculated moisture content was 210 ppm.

EXAMPLE 3

Measurement of moisture content in CNT-based paste. A CNT-based paste was produced using method described in U.S.2011/0171364. In a moisture controlled environment, 8 gram of paste sample was placed in a sealable container. 60 gram of ethyl acetate was then added to the paste followed by stirring. After CNTs were completely precipitated to the bottom of container, a pipette was used to obtain 300 μL of clear solution. This solution was then injected into Karl Fischer reagent and the reaction allowed to complete. The moisture content is then obtained via a stoichiometric reaction.

The moisture content is calculated as:
$C_1$=weight fraction of first solvent in paste sample
$W_2$=weight of second solvent in paste sample
M=weight of paste sample before second solvent added
$S_0$=weight fraction of water in mixed solvent sample as analyzed
$S_2$=weight fraction of water in second solvent—as added to paste sample
Wp=weight fraction of water in paste—before second solvent added.

$$Wp = \frac{S_0 \times [M \times C_1 + W_2] - S_2 \times W_2}{M} \quad (1)$$

TABLE 3

|  | Paste (g) | Ethyl Acetate (g) | Dilution Times | Measured Moisture (ppm) | | | |
|---|---|---|---|---|---|---|---|
|  |  |  |  | Test 1 ppm | Test 2 ppm | Test 3 ppm | Average Value |
| Sample 1 | 8.3 | 61.73 | 8.437 | 1562 | 1497 | 1438 | 1,501 |
| Sample 2 | 8.57 | 66.46 | 8.755 | 1684 | 1616 | 1520 | 1,605 |
| Sample 3 | 8.8 | 65.62 | 8.457 | 1682 | 1788 | 1746 | 1,737 |

The classic laboratory method of measuring high level moisture in solid or semi-solid materials is loss on drying (LOD). In this technique a sample of material is weighed, heated in an oven for an appropriate period, cooled in the dry atmosphere of a desiccator, and then reweighed. If the volatile content of the solid is primarily water, the LOD technique gives a good measure of moisture content. An accurate method for determining the amount of water is the Karl Fischer titration, developed in 1935 by the German chemist whose name it bears. This method detects only water, contrary to loss on drying, which detects any volatile substances.

From the Annual Book of ASTM (American Society for Testing and Materials) Standards, the total evaporable moisture content in Aggregate (C 566) is calculated with the formula:

$$p = \frac{W - D}{D} \quad (2)$$

where p is the fraction of total evaporable content of sample, W is the mass of the original sample, and D is mass of dried sample. Based on the know amount of solvent added the water content can be calculated as "excess".

In some embodiments a method of preparing a battery electrode coating using a paste composition as disclosed herein comprises the steps: mixing the paste composition with lithium ion battery materials; coating the paste onto a metallic film to form an electrode for a lithium ion battery and removing excess or at least a portion of the liquid from the coating; optionally, a method further comprises the step of mixing a polymeric binder with a liquid vehicle before mixing the paste composition with lithium ion battery materials; optionally, a method uses a polymeric binder chosen from a group consisting of polyethylene, polypropylene, polyamide, polyurethane, polyvinyl chloride, polyvinylidene fluoride, thermoplastic polyester resins, and mixtures thereof and is less than about 5% by weight of the paste composition; optionally, a method utilizes spherical carbon nanotube agglomerates fabricated in a fluidized bed reactor as described in Assignee's inventions U.S. Pat. No. 7,563,427, and U.S. Applications 2009/0208708, 2009/0286675, and U.S. Ser. No. 12/516,166. Optionally, a paste composition as disclosed herein utilizes spherical carbon nanotube agglomerates fabricated in a fluidized bed reactor as described in Assignee's inventions U.S. Pat. No. 7,563,427, and U.S. Applications 2009/0208708, 2009/0286675, and U.S. Ser. No. 12/516,166. An alternate method of making paste comprises drying carbon nanotubes at 110° C. and drying dispersant or binder at 60° C. under vacuum, carrying out dispersion process under nitrogen blanket, and sealing off product using a moisture proof bag, e.g. aluminum foil-lined plastic bag.

EXAMPLE 4

Moisture Control and Content from Disclosed Process

A paste is prepared using disclosed methods of the instant invention. In an example, 5 grams of carbon nanotubes are firstly placed in a vacuum oven and kept at 110° C. for a period of time, optionally, 10 hours. A selected dispersant is also dried under vacuum at appropriate temperatures for removing moisture based upon the selected dispersant's boiling point and vapor pressure versus water. In some embodiments N-methyl pyrrolidone is used as-is. The moisture content measured from such a paste made with disclosed process is less than 400 ppm. In some embodiments an acceptable water content is less than about 1000 ppm.

In some embodiments an electrode material composition, or electrode material, for coating to a metallic current collector or metal conductor for a lithium battery comprises multi-walled carbon nanotubes in an agglomerate; electrode active materials chosen from a group consisting of lithium, oxygen, phosphorous, sulphur, nitrogen, nickel, cobalt, manganese, vanadium, silicon, carbon, graphite, aluminum, niobium, titanium and zirconium and iron; a dispersant chosen from a group consisting of poly(vinylpyrrolidone) (PVP), poly(styrene sulfonate) (PSS), poly(phenylacetylene) (PAA), poly(meta-phenylenevinylene) (PmPV), polypyrrole (PPy), poly(p-phenylene benzobisoxazole) (PBO), natural polymers, amphiphilic materials in aqueous solutions, anionic aliphatic surfactant, sodium dodecyl sulfate (SDS), cyclic lipopeptide biosurfactant, surfactin, water-soluble polymers, carboxyl methyl cellulose, hydroxyl ethyl cellulose, poly(vinyl alcohol), PVA, sodium dodecyl sulfate, SDS, n-methylpyrrolidone, polyoxyethylene surfactant, poly(vinylidene fluoride), PVdF, carboxyl methyl cellulose (CMC), hydroxyl ethyl cellulose (HEC), polyacrylic acid (PAA), polyvinyl chloride (PVC) and combinations thereof; and a polymeric binder chosen from a group consisting of polyethylene, polypropylene, polyamide, polyurethane, polyvinyl chloride, polyvinylidene fluoride, thermoplastic polyester resins and mixtures thereof and is less than about 0.5% to 5% by weight of the electrode material composition wherein the electrode active material is 30-60% by weight, the carbon nanotubes are present in a range from about 0.2 to about 5% by weight, and the dispersant is less than 0.1 to 2% by weight before coating to a metallic current collector; after coating and drying the electrode active material is more than 80% by weight and in some embodiments more than 90% by weight; optionally, an electrode material composition comprises carbon nanotube agglomerates made in a fluidized bed reactor; optionally, an electrode material composition comprises carbon nanotube agglomerates with a maximum dimension from about 0.5 to about 1000 microns; optionally, an electrode material composition comprises carbon nanotubes with a diameter from about 4 to about 100 nm; optionally, an electrode material comprises carbon nanotubes wherein the tap density of the carbon nanotube agglomerates is greater than about 0.02 g/cm$^3$; optionally, an electrode material comprises material wherein the bulk resistivity of the material is less than 10 ohm-cm; optionally less than less than 1 ohm-cm; optionally less than 0.1 ohm-cm.

In some embodiments a method for measuring the water content of a fluid or paste comprising multi-walled carbon nanotube agglomerates, dispersant and polymeric binders comprises the steps; selecting a fluid or paste comprising a first solvent; adding a second solvent to the fluid or paste; precipitating the multi-walled carbon nanotube agglomerates from the first and second solvent solution; taking a sample of the first and second solvent; measuring the water content of the sample; wherein multi-walled carbon nanotube agglomerates are dispersed in the first solvent and do not disperse in the second solvent and the second solvent is miscible with the first solvent; optionally, the weight ratio of the first solvent to the second solvent is between about 2:1 and about 1:10; optionally, the measuring of the water content is done by one or more of the techniques consisting of solvent evaporation, Karl-Fischer titration, coulometric titration, and volumetric titration; optionally, the second solvent is chosen from a group consisting of ethyl acetate, acetone, ethers, alcohols, ketones, esters and mixtures thereof; optionally, the first solvent is chosen from a group consisting of poly(vinylpyrrolidone) (PVP), poly(styrene sulfonate) (PSS), poly(phenylacetylene) (PAA), poly(meta-phenylenevinylene) (PmPV), polypyrrole (PPy), poly(p-phenylene benzobisoxazole) (PBO), natural polymers, amphiphilic materials in aqueous solutions, anionic aliphatic surfactant, sodium dodecyl sulfate (SDS), cyclic lipopeptide biosurfactant, surfactin, water-soluble polymers, carboxylmethyl cellulose, hydroxyl ethyl cellulose, poly(vinyl alcohol), PVA, sodium dodecyl sulfate, SDS, n-methylpyrrolidone, polyoxyethylene surfactant, poly(vinylidene fluoride), PVdF, carboxyl methyl cellulose (CMC), hydroxyl ethyl cellulose (HEC), polyacrylic acid (PAA), polyvinyl chloride (PVC) and combinations thereof; optionally, the tap density of the carbon nanotube agglomerates is greater than about 0.02 g/cm$^3$; optionally, the fluid or paste material composition comprises a polymeric binder chosen from a group consisting of polyethylene, polypropylene, polyamide, polyurethane, polyvinyl chloride, polyvinylidene fluoride, thermoplastic polyester resins, and mixtures thereof and is less than about 5% by weight of the fluid or paste composition; optionally, the multi-walled carbon nanotube agglomerates, dispersant and polymeric binders are formed into a fluid or paste wherein the multi-walled carbon nanotube agglomerates amount are present in the range of about 1 to 15% by weight of the fluid or paste; optionally, the multi-walled carbon nanotube agglomerates, dispersant and polymeric binders are formed into a fluid or paste wherein the multi-walled carbon nanotube agglomerates amount are present in the range of about 0.2 to 5% by weight of the fluid or paste.

In some embodiments a method for measuring the water content of a fluid or paste comprises the steps; selecting a fluid or paste comprising a first solvent and a first component wherein the first solvent wets the surface of the first component; adding a second solvent to the fluid or paste; precipitating the first component from the first and second solvent solution; taking a sample of the first and second solvent; measuring the water content of the sample; wherein the first component is dispersed in the first solvent and does not disperse in the second solvent and the second solvent is miscible with the first solvent; optionally, the weight ratio of the first solvent to the second solvent is between about 2:1 and 1:10.

In some embodiments a battery comprises a paste comprising multi-walled carbon nanotube agglomerates present in the range of about 1 to 15% by weight wherein the tap density of the carbon nanotube agglomerates is greater than about 0.02 g/cm$^3$ and the water content of the paste prior to incorporation in the battery has been measured by the method of the disclosed invention to be less than about 1000 ppm by weight.

In the previous description, numerous specific details are set forth to provide a thorough understanding of the present invention. However, it will be apparent to one of ordinary skill in the art that the invention may be practiced without these particular details. In other instances, methods, procedures, and components that are well known to those of ordinary skill in the art are not described in detail to avoid obscuring aspects of the present invention. In cases where reference is made to "an embodiment" or "one embodiment" or "some embodiments", it is understood that embodiments may comprise one or more of the inventive features and/or limitations presented in the entire specification for all exemplary embodiments without regard to how a particular embodiment is described.

It will also be understood that, although the terms first, second, etc. may be used herein to describe various elements, these elements should not be limited by these terms. These terms are only used to distinguish one element from another. For example, a first layer could be termed a second layer, and, similarly, a second layer could be termed a first layer, without departing from the scope of the present invention.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms used in disclosing embodiments of the invention, including technical and scientific terms, have the same meaning as commonly understood by one of ordinary skill in the art to which this invention belongs, and are not necessarily limited to the specific definitions known at the time of the present invention being described. Accordingly, these terms can include equivalent terms that are created after such time. It will be further understood that terms, such as those defined in commonly used dictionaries, should be interpreted as having a meaning that is consistent with their meaning in the present specification and in the context of the relevant art and will not be interpreted in an idealized or overly formal sense unless expressly so defined herein. All publications, patent applications, patents, and other references mentioned herein are incorporated by reference in their entirety.

While the invention has been described by way of example and in terms of the specific embodiments, it is to be understood that the invention is not limited to the disclosed embodiments. To the contrary, it is intended to cover various modifications and similar arrangements as would be apparent to those skilled in the art. Therefore, the scope of the appended claims should be accorded the broadest interpretation so as to encompass all such modifications and similar arrangements. All publications, patents, and patent applications cited herein are hereby incorporated by reference in their entirety for all purposes.

What we claim is:

1. A method for measuring the water content of a fluid or paste comprising multi-walled carbon nanotube agglomerates, dispersant and polymeric binder, the method comprising the steps:

selecting the fluid or paste comprising the multi-walled carbon nanotube agglomerates, the dispersant and the polymeric binders and further comprising a first solvent, wherein the multi-walled carbon nanotube agglomerates, the dispersant and the polymeric binder of the fluid or paste are dispersed in the first solvent;

adding a second solvent to the fluid or paste such that the second solvent is more than about 25% by volume or weight ratio of the total solvent mixture of the first solvent and the second solvent and wherein the multi-walled carbon nanotube agglomerates do not disperse in the total solvent mixture and the second solvent is miscible with the first solvent;

precipitating the multi-walled carbon nanotube agglomerates from the total solvent mixture, thereby leaving a supernatant;

taking a sample of the supernatant; and measuring the water content of the sample.

2. The method of claim 1 wherein the weight ratio of the first solvent to the second solvent in the total solvent mixture is between about 2:1 and about 1:10.

3. The method of claim 1 wherein the measuring of the water content is done by one or more of the techniques consisting of solvent evaporation, Karl-Fischer titration, coulometric titration, and volumetric titration.

4. The method of claim 1 wherein the second solvent is chosen from a group consisting of ethers, alcohols, ketones, esters and mixtures thereof.

5. The method of claim 4 wherein the ketones include acetone and the esters include ethyl acetate.

6. The method of claim 1 wherein the first solvent is chosen from a group consisting of poly(vinylpyrrolidone) (PVP), poly(styrene sulfonate) (PSS), poly(phenylacetylene) (PAA), poly(meta-phenylenevinylene) (PmPV), polypyrrole (PPy), poly(p-phenylene benzobisoxazole) (PBO), natural polymers, amphiphilic materials in aqueous solutions, anionic aliphatic surfactant, sodium dodecyl sulfate (SDS), cyclic lipopeptide bio surfactant, surfactin, water-soluble polymers, carboxyl methyl cellulose, hydroxyl ethyl cellulose, poly(vinyl alcohol), (PVA), n-methylpyrrolidone, polyoxyethylene surfactant, poly(vinylidene fluoride), (PVdF), carboxyl methyl cellulose (CMC), hydroxyl ethyl cellulose (HEC), polyacrylic acid (PAA), polyvinyl chloride (PVC) and combinations thereof.

7. The method of claim 1 wherein the tap density of the carbon nanotube agglomerates is greater than about 0.02g/cm$^3$.

8. The method of claim 1 wherein the a polymeric binder is chosen from a group consisting of polyethylene, polypropylene, polyamide, polyurethane, polyvinyl chloride, polyvinylidene fluoride, thermoplastic polyester resins, and mixtures thereof and the polymeric binder is less than about 5% by weight of the fluid or paste.

9. The method of claim 1 wherein the multi-walled carbon nanotube agglomerates are present in the fluid or paste in the range of about 1 to 15% by weight of the fluid or paste.

10. The method of claim 1 wherein the multi-walled carbon nanotube agglomerates are present in the fluid or paste in the range of about 0.2 to 5% by weight of the fluid or paste.

* * * * *